US012121445B2

(12) United States Patent
Hafez et al.

(10) Patent No.: US 12,121,445 B2
(45) Date of Patent: Oct. 22, 2024

(54) TOOL FOR CUSTOM-MADE INSTRUMENTS AND IMPLANT FOR ARTIFICIAL KNEE JOINT OF DOGS

(71) Applicant: Mahmoud Alm El Din Hafez, Giza (EG)

(72) Inventors: Mahmoud Alm El Din Hafez, Giza (EG); Ashraf Shamaa, Giza (EG); Ahmed Abdel Moghny Salem, Giza (EG); Rania Kashif, October (EG); Elham Hassan, Giza (EG)

(73) Assignee: Mahmoud Hafez, Giza (EG)

( * ) Notice: Subject to any disclaimer, the term of this patent is extended or adjusted under 35 U.S.C. 154(b) by 158 days.

(21) Appl. No.: 17/154,463

(22) Filed: Jan. 21, 2021

(65) Prior Publication Data

US 2021/0177604 A1     Jun. 17, 2021

Related U.S. Application Data

(63) Continuation of application No. 15/549,178, filed as application No. PCT/EG2015/000004 on Feb. 8, 2015, now abandoned.

(51) Int. Cl.
*A61F 2/30* (2006.01)
*A61B 17/15* (2006.01)
*A61F 2/38* (2006.01)

(52) U.S. Cl.
CPC ........ *A61F 2/30942* (2013.01); *A61B 17/155* (2013.01); *A61B 17/157* (2013.01); *A61F 2/38* (2013.01); *A61F 2002/307* (2013.01); *A61F 2/3836* (2013.01)

(58) Field of Classification Search
CPC ... A61B 17/154; A61B 17/155; A61B 17/157; A61F 2/30942; A61F 2/38–389; A61F 2002/3809–3895
See application file for complete search history.

(56) References Cited

U.S. PATENT DOCUMENTS

| 4,834,081 | A | * | 5/1989 | Van Zile | A61F 2/461 606/99 |
| 5,019,103 | A | * | 5/1991 | Van Zile | A61F 2/389 623/20.34 |
| 5,207,711 | A | * | 5/1993 | Caspari | A61F 2/38 623/20.3 |
| 5,385,529 | A | * | 1/1995 | Koch | A61G 11/00 600/549 |

(Continued)

*Primary Examiner* — Matthew J Lawson
(74) *Attorney, Agent, or Firm* — Dickinson Wright PLLC; Andrew D. Dorisio (57) ABSTRACT

Total knee replacement is the standard treatment for advanced knee osteoarthritis. An improved method of treating an osteochondral defect for knee osteoarthritis of dogs is provided, which is a composite tissue for treating or preventing disease, disorder, or condition associated with an osteochondral defect with new technique. The new technique of custom made instruments and implants for dog and small animals is applied for different breeds of dogs regardless of their sizes and weights. The tool is a custom made instrument, which is based on capture of image based (CT of computed X-ray) to be transferred to electronic 3D model and apply 3D preoperative planning to design the tools are used to perform the knee surgery.

12 Claims, 8 Drawing Sheets

Femoral Implant, Isometric View (56) References Cited

U.S. PATENT DOCUMENTS

| | | | | |
|---|---|---|---|---|
| 2004/0002766 A1* | 1/2004 | Hunter | ............ | A61L 27/306 |
| | | | | 623/22.17 |
| 2005/0055100 A1* | 3/2005 | Lewis | ............ | A61F 2/38 |
| | | | | 623/20.28 |
| 2010/0049195 A1* | 2/2010 | Park | ............ | A61B 34/10 |
| | | | | 700/98 |
| 2011/0029091 A1* | 2/2011 | Bojarski | ............ | A61F 2/389 |
| | | | | 606/86 R |

* cited by examiner

Figure 1: Tibial Implant

All views (1-A, 1-B)

Figure 1-A Tibial Implant, Isometric View

Figure 1-B Tibial Implant, Front View

Figure 2: Femoral Implant

All views ( 2-A, 2-B )

Figure 2-A Femoral Implant, Isometric View

Figure 2-B Femoral Implant, Side View

Figure 3: Tibial Tool

All views ( 3-A, 3-B, 3-C, 3-D, 3-E, 3-F )

Figure 3-A Tibial Tool, Front View

Figure 3-B Tibial Tool, Side View

Figure 3-C Tibial Tool, Top View

Figure 3-D Tibial Tool, Isometric View

Figure 3-E Tibial Tool on a bone model, Isometric View

Figure 3-F Tibial Tool on a bone model, Front View

Figure 4: Femoral Tool

All views ( 4-A, 4-B, 4-C, 4-D, 4-E, 4-F )

Figure 4-A Femoral Tool, Front View

Figure 4-B Femoral Tool, Side View

Figure 4-C Femoral Tool, Top View

Figure 4D

Figure 4-E Femoral Tool on a bone model, Isometric View

Figure 4-F Femoral Tool on a bone model, Front View

TOOL FOR CUSTOM-MADE INSTRUMENTS AND IMPLANT FOR ARTIFICIAL KNEE JOINT OF DOGS

This application claims the benefit of U.S. Ser. No. 15/549,178, the disclosure of which is incorporated herein by reference.

TECHNICAL FIELD

Total knee arthroplasty (TKA) is a common procedure for human and it is the standard surgical treatment for severe arthritis. The standard technique for human knees is to perform the surgery using reusable instruments and on shelf implants that has 4-8 different sizes. In animals, there are different species and in the same animal there are different breads. For example, there could be more than 100 different breeds of dogs in a single country. Each bread has different sizes. This make impossible to have a large inventory of implant sizes to cover all variations. For this reason, this operation (TKA) is not common in animals.

BACKGROUND OF THE INVENTION

The increased incidence of knee osteoarthritis calls for continuous development of surgical techniques and exploiting cutting-edge technology for improving knee replacement methods to obtain full physical fitness and knee joint health. The current total knee arthroplasty (TKA) technique is expensive and company specific, which is a significant disadvantage that limits the wide-spread application and availability of TKA. Further, the current technique is limited to the straight-forward knee replacement and not for complex cases of severe intra-/extra-articular deformity. TKA has been increasingly demanding in animals due to increased rate of accidents and osteogenic tumors.

DISCLOSURE OF INVENTION

The invention is a tool for preparing a stifle for dogs undergoing TKA. This should provide knee prosthesis with universal applicability, fitting to the exact anatomical structure of the stifle. The universal tool would replace any commercially and currently available knee implant. It should also help in planning TKA and designing knee prosthesis for humans in the near future.

The current invention involves fabricating guiding and articulating components. The guiding components are known in literature as patient-specific instrumentation (PSI) which eliminates preoperative coupling with other surgical instruments (e.g., drills, sleeves, intramedullary rods and jigs). The preoperative plan is transferred to virtual and then physical components for accurate sizing, alignment and rotation. The bone-machining is carried out through specific paths which are multidirectional but accurately positioned to prevent any intersection. It helps to target bony surfaces directly away from cartilage or other soft tissues.

The articulating components should compose of 3 parts: 2 metallic parts (tibial and femoral) and 1 plastic part at their intersection which simulates the natural interosseous cartilage. They are tailored for each case specifically according to image-based 3D preoperative planning (CT, MRI or computed X-ray) which are converted to physical components using computer-aided manufacturing such as computer numerical control, additive manufacturing, rapid prototyping and 3D printing. These subject-specific components allow bone preparation and integration and can be placed in a unique and secure position.

Surgical simulation of bone cutting and prosthesis positioning is performed using virtual templates. The final prosthesis is manufactured and built of mesh, porous metallic material (cobalt chromium) to allow for osteointegration.

The same technique can be applied for other knee procedures such as unicompartmental, bicondylar and patellofemoral arthroplasty. It also serves in treating non-standard cases.

DESCRIPTION OF PATENT

The current invention involves planning for TKA with the very early step through digital templating (through digital radiograph, CT scan and MRI) to design the prosthetic components of TKA virtually. The design should planned according to proper designation criteria including calculated magnification, angulation and alignment. This is the first step for preparing the subject's stifle for TKA.

The virtual deign is transformed into physical components which are the tool that is produced through medical rapid prototyping (aka, additive manufacturing or 3D printing). The physical components are thus tailored specifically for the subject according to the collected measures from radiographs. Simulation of surgery would lead to accurate positioning of the prosthetic components.

The tool should overcome the under sizing or overhang that usually take place with the currently used knee implants. The prosthetic components are the bone-like femoral and tibial parts (metallic components) and the middle plastic part that resembles natural knee cartilage.

This technology is suitable for any knee regardless of different shapes, configurations and anatomy. The prosthetic components are made of durable, biocompatible and hybrid materials containing metallic and composite parts which are produced through bone-machining steps including sizing, alignment, bone cutting and positioning.

DESCRIPTION OF DRAWINGS

All views (1-A, 1-B)

Figure 1:
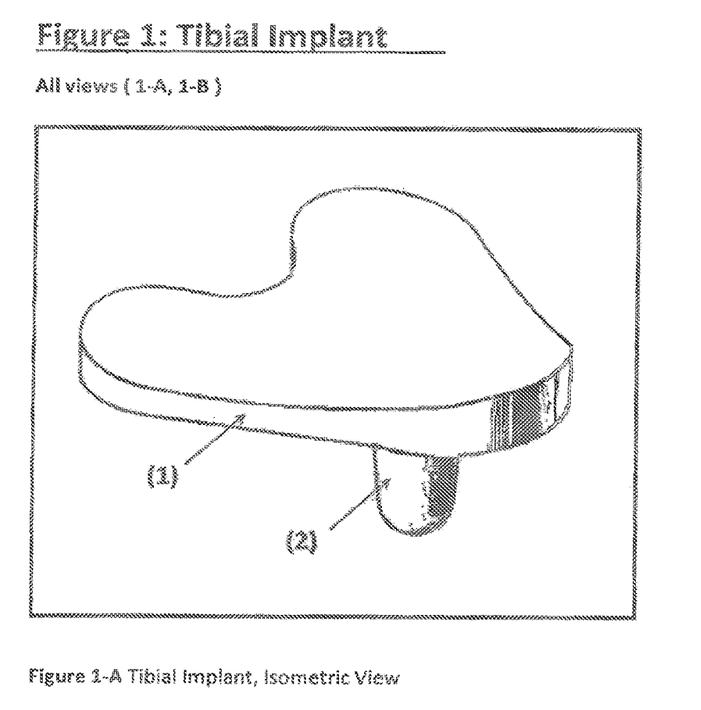
FIG. 1: Tibial Implant

The figure has two views of the tibial implant in isometric and front view. The tibial implant has an articular surface (label no. 1) matching with femoral implant surface, and a stem with tapered shape (label no. 2).

All views (2-A, 2-B)

Figure 2:
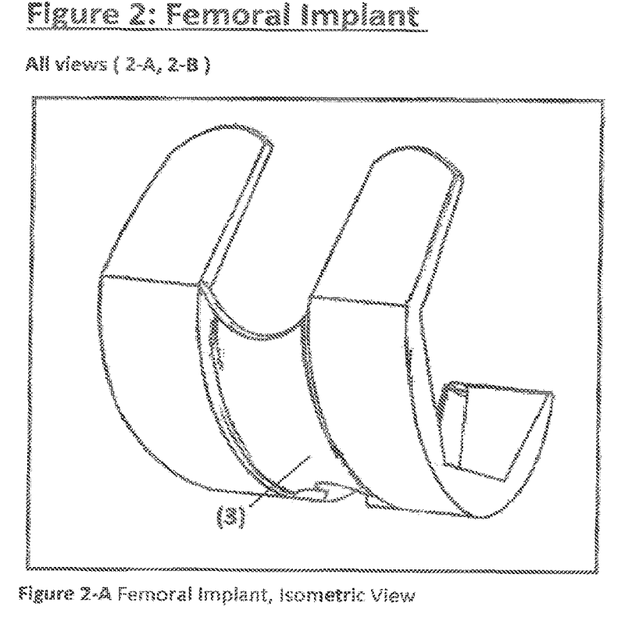
FIG. 2: Femoral Implant
Figure 3:
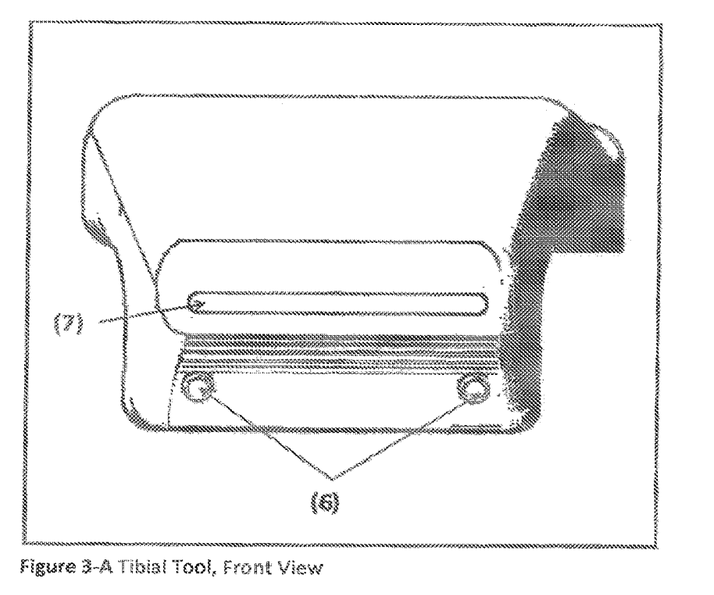
FIG. 3: Tibial Tool Part.
Figure 4:
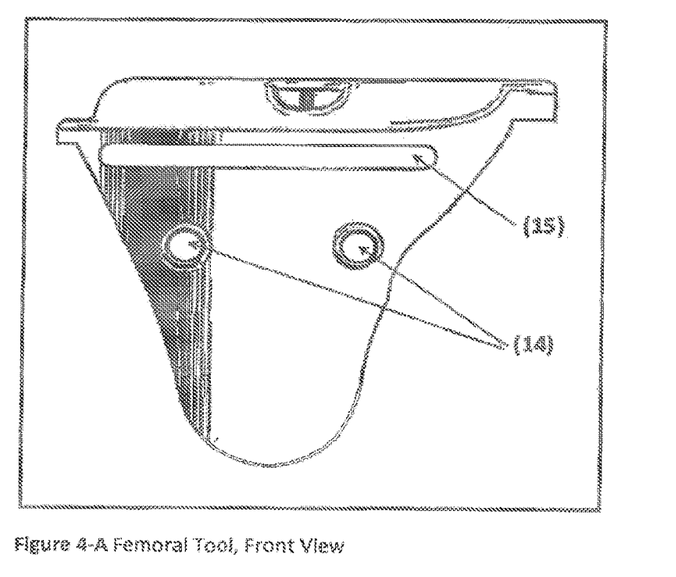
FIG. 4: Femoral Tool Part.
Figure 4D:
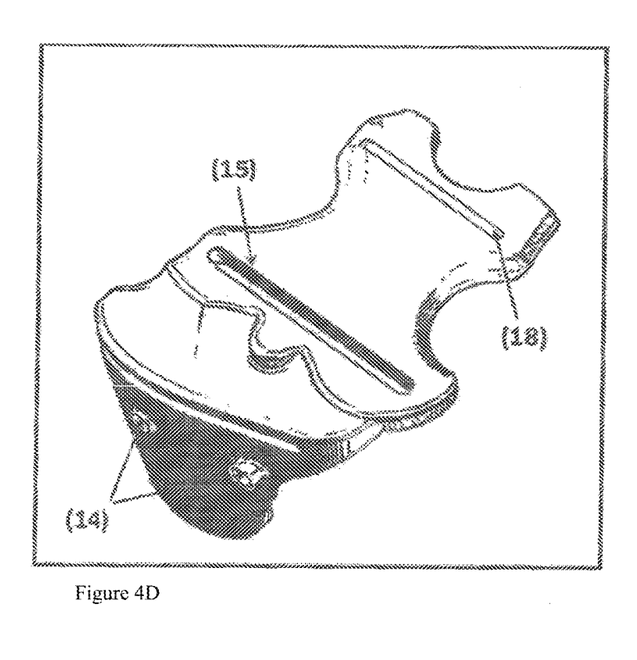

The figure has two views of the femoral implant in isometric and side view. The femoral implant has a central groove with an articular surface (label no. 3) matching with patella track surface. The femoral implant has four femoral cut surfaces for distal, anterior, posterior, and anterior chamfer (label no. 5), and two pegs with tapered shape (label no. 4). As can be understood from FIG. 2, the femoral component is characterized by an external groove with a fork shape not extending to a trochlea, so as to decrease pain of trochlea area bone rubbing on a surface of the implant.

All views (3-A, 3-B, 3-C, 3-D, 3-E and 3-F)

The figure has several views of the tibial tool from 3-A to 3-F. the tibial tool was designed to have two surfaces for matching with the tibia bone (label no. 9 and 10), the tibial tool has four fixation holes located as two holes in anterior side (label no. 6) and two holes in the top side (label no. 8).

The tibial tool has a slit for performing of tibial cut (label no. 7) and a central hole in the top surface for drilling of the stem (label no. 11). Views (3-E and 3-F) shows the tibial tool over the tibia bone.

All views (4-A, 4-B, 4-C, 4-D, 4-E and 4-F)

The figure has several views of the femoral tool from 4-A to 4-F. the femoral tool was designed to have two surfaces for matching with the femur bone (label no. 16 and 17), the femoral tool has two luge holes for drilling of pegs (label no. 14). The femoral tool has a slits to performing the femoral cuts (label no. 15 and 18). Views (4-E and 4-F) shows the femoral tool over the femur bone.

REFERENCES

1. US 2005/0055100 A1 (Lewis et al.) 10 Mar. 2005.
2. WO 2014198279 (HAFEZ, Mahmoud Aim EL Din) 18 Dec. 2014.
3. U.S. Pat. No. 8,435,246 B2 (Michael G. Fisher, Anthony K. Hedley, T. NEVINS, Kevin M. Cordes) 7 May 2013

The invention claimed is:

1. A custom made implant for use on a dog or small animal in a knee arthroplasty (TKA) surgery, the knee including a trochlea, comprising:
 a tibial component;
 a femoral component; and
 a plastic part positioned at an intersection of said tibial and femoral components, said plastic part simulating natural articular cartilage such that said tibial component articulates with said femoral component due to said plastic part;
 wherein said femoral component comprises a fork shape adapted to not extend to the trochlea, so as to decrease pain of bone in an area of the trochlea rubbing on the implant, and an external groove extending to a space located between bifurcations of the fork shape of the femoral component;
 wherein the custom made implant is based on a planning of virtual surgery of the TKA; and
 wherein the custom made implant provides an artificial knee prosthesis, fitting to an anatomical structure of a stifle of the dog or small animal undergoing the TKA surgery.

2. The custom made implant of claim 1, wherein said femoral component includes a plurality of internal surfaces for matching a femur bone anatomy of the stifle and adapted to fit a distal cut, an anterior cut, an anterior chamfer cut and a posterior cut of the femur.

3. The custom made implant of claim 1, wherein said femoral component includes two anterior pegs for extending between epicondyles, each of the pegs having a tapered shape.

4. The custom made implant of claim 1, wherein the external groove has a width corresponding to a width of the space between the bifurcations.

5. The custom made implant of claim 1, wherein said tibial component is heart-shaped and adapted to fit a tibia bone in a cutting area following resection thereof.

6. The custom made implant of claim 1, wherein the tibial or femoral components are fabricated of mesh and porous metallic material to allow for osteointegration.

7. A custom made implant for use on a dog or small animal in a knee arthroplasty (TKA) surgery, the knee including a trochlea, comprising:
 a tibial component including a stem having an axis orthogonal to a surface of the tibial component;
 a femoral component, wherein said femoral component comprises a fork shape adapted to not extend to the trochlea, so as to decrease pain of bone in an area of the trochlea rubbing on the implant and an external groove extending to a space located between bifurcations of the fork shape of the femoral component; and
 a plastic part positioned at an intersection of said tibial and femoral components, said plastic part simulating natural articular cartilage such that said tibial component articulates with said femoral component due to said plastic part;
 wherein the custom made implant is based on a planning of virtual surgery of the TKA; and
 wherein the custom made implant provides an artificial knee prosthesis, fitting to an anatomical structure of a stifle of the dog or small animal undergoing the TKA surgery.

8. The custom made implant of claim 7, wherein said femoral component includes a plurality of internal surfaces for matching a femur bone anatomy of the stifle and adapted to fit a distal cut, an anterior cut, an anterior chamfer cut and a posterior cut of the femur.

9. The custom made implant of claim 7, wherein said femoral component includes two anterior pegs for extending between epicondyles, each of the pegs having a tapered shape.

10. The custom made implant of claim 7, wherein the external groove has a width corresponding to a width of the space between the bifurcations.

11. The custom made implant of claim 7, wherein said tibial component is heart-shaped and adapted to fit a tibia bone in a cutting area following resection thereof.

12. The custom made implant of claim 7, wherein the tibial or femoral components are fabricated of mesh and porous metallic material to allow for osteointegration.

* * * * *